United States Patent [19]

Hussain

[11] Patent Number: 4,929,785
[45] Date of Patent: May 29, 1990

[54] PROCESS FOR PREPARING DIPHENYLALKANE

[75] Inventor: Saadat Hussain, Baton Rouge, La.

[73] Assignee: Ethyl Corporation, Richmond, Va.

[21] Appl. No.: 326,096

[22] Filed: Mar. 20, 1989

[51] Int. Cl.$^5$ .......................... C07C 2/02; C07C 2/72; C07C 1/20
[52] U.S. Cl. .................................. 585/426; 585/428; 585/469
[58] Field of Search .................... 585/469, 426, 428

[56] References Cited

U.S. PATENT DOCUMENTS 2,392,595  12/1941  Kharasch ............................ 585/428

OTHER PUBLICATIONS

Steric and Complexation Factors in Hydrogen Abstraction from 1-Phenylalkanes and α, ω-Diphenylalkanes, Newkirk et al., Tetrahedron 28: 449–454 (1972).
Buu-Hoi et al., "The Reaction of α-Halogenated Arylalkanes with Metal Powders in Hydroxylated Media", J. Org. Chem., vol. 14, pp. 1023–1035 (1949).
Ogata et al., "A Note on the Dechlorination Condensation of Benzal Chloride and Benzotrichloride by Iron and Water", J. Org. Chem., vol. 21, pp. 1170–1171 (1956).
Ogata et al., "The Dechlorination of Some Organic Compounds with Iron Powder as Dechlorinating Agent", Chem. Abstract, vol. 43, 2194d (1949).
Wada et al., "The Reductive Coupling Reactions of Benzyl Chloride by Copper (I) Complexes", Bull. of the Chem. Soc. of Japan, vol. 41, pp. 3001–3007 (1968).
Onuma et al., "The Reductive Coupling Reactions of Some Chloromethylbenzene Derivatives with Iron (II) and Copper (I) Complexes", Bull. of the Chem. Soc. of Japan, vol. 43, pp. 836–841 (1970).
Ebert et al., "Preparation of Aryl, Alkynyl, and Vinyl Organocopper Compounds by the Oxidative Addition of Zerovalent Copper to Carbon-Halogen Bonds", J. Org. Chem., vol. 53, pp. 4482–4488, 1988.

*Primary Examiner*—H. M. S. Sneed
*Assistant Examiner*—J. Saba
*Attorney, Agent, or Firm*—Edgar E. Spielman, Jr.

[57] ABSTRACT

A process is disclosed for producing diphenylalkanes, which process comprises the formation of a reaction mass comprising a (1) solvent, (2) iron, (3) copper, Cu(I) salt or a mixture thereof, and (4) phenylalkylhalide, and maintaining this reaction mass at a temperature of at least 40° C. until diphenylalkane is formed.

21 Claims, No Drawings

PROCESS FOR PREPARING DIPHENYLALKANE

BACKGROUND OF THE INVENTION

This invention relates to a process for preparing diphenylalkanes.

Brominated diphenylalkanes, e.g. decabromodiphenylethane, are recognized flame retardants for use in various thermoplastic formulations. These flame retardants can be formed by partially or totally brominating diphenylalkane with a brominating agent, e.g. $Br_2$ or BrCl, in the presence of a Lewis acid catalyst.

Despite the efficacy of brominated diphenylalkanes as flame retardants, their acceptance as a commercially viable product has been hampered by their cost. The largest factor contributing to their cost is the cost of the starting material, diphenylalkane. Most processes for producing diphenylalkane are characterized by their low yields and/or by their complexity. For example, diphenylethane can be produced by reacting benzyl chloride in an aqueous medium with iron powder (99.9+% pure iron). While this reaction is relatively simple, the yield is only about 16%. Higher yields can be obtained by other processes, but such yields come with a loss in process simplicity and the use of more expensive reagents. Exemplary of such processes, is the process described by Wada et al in "The Reductive Coupling Reactions of Benzyl Chloride by Copper (I) Complexes", *Bulletin of the Chemical Society of Japan*, Vol. 41, Pages 3001–3007 (1968). This process effects the coupling of benzyl chloride by reacting same with a Cu(I) complex. The Cu(I) complex is obtained by providing a complexing agent, e.g. ethylenediamine, diethylenetriamine, triethylenetetramine, acetylacetone, or EDTA to the reactin mixture which contains cuprous chloride, a reaction solvent and benzyl chloride.

It is therefore an object of this invention to provide an economical process for producing diphenylalkane which is characterized by good yields, relatively inexpensive reagents, and simplicity.

THE INVENTION

This invention relates to a process for preparing diphenylalkanes, which process comprises: (a) forming a reaction mass which contains; (i) iron, (ii) copper, a CU(I) salt of an inorganic or organic acid or a mixture of copper and such a Cu(I) salt, (iii) a phenylalkylhalide, and (iv) a solvent in which Fe(II) halide salts are at least substantially soluble; and (b) maintaining the reaction mass at a temperature of at least 40° C. until the diphenylalkane is formed. Preferably, the reaction mass contains an amount of solvent which is sufficient to solubilize substantially all of any Fe(II) halide salt formed during the process.

While the foregoing process is capable of producing diphenylalkanes in high yields with the use of copper or Cu(I) salts, it has been found that even higher yields can be obtained by using the mixture of copper and the Cu(I) salts.

For the purposes of this invention, the diphenylalkanes produced by the process of this invention can be represented by the formula:

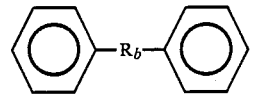

wherein R is a methylene group and b is 2, 4, 6, 8, or 10. Exemplary of suitable diphenylalkanes are 1,2-diphenylethane, 1,4-diphenylbutane, 1,6-diphenylhexane, 1,8-diphenyloctane, 1,10-diphenyldecane. A most preferred diphenylalkane product is 1,2-diphenylethane as this product is used in preparing decabromodiphenylethane, a recognized and valuable flame retardant material.

The phenylalkylhalide constituent of the reaction mass can be represented by the formula:

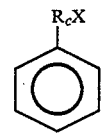

wherein $c = \frac{1}{2} b$, X is a halide radical, and R is as defined above. Of the halide radicals, the chloride radical is preferred. Exemplary phenylalkylhalides are benzyl chloride, beta-phenylethylchloride, 1-chloro-3-phenylpropane, 1-chloro-4-phenylbutane, 1-chloro-5phenylpentane, and the like. The preferred phenylalkylhalide is benzyl chloride as it is readily available and will yield the preferred diphenylethane product.

The iron utilized in the process of this invention is elemental iron and can be provided to the reaction mass as particulate iron. Powdered iron is preferred as it is readily available. Should the iron contain iron oxide, hydrogen can be utilized to reduce this contaminant to iron.

To maximize the yield of diphenylalkane, the minimum amount of iron that should be used in the reaction mass is at least about 0.50 mol of iron per mol of phenylalkylhalide, which ratio satisfies the stoichiometric requirements of the reaction. Less than the stoichiometric amount of irom can be used, but there will be a reduction in product yields. More than the stoichiometric amount of irom can also be used, but the reaction economics may suffer and color problems can occur in the product.

Although the function, in the reaction, of the copper and the Cu(I) salt is not completely understood, it is believed that they singularly and in combination catalyze and/or promote the reaction between the iron and the phenylalkylhalide. The surprising aspect of this catalyzation and/or promotion, is that it occurs without the need of the before-mentioned complexing agents. This is not to say such complexing agents may not be used in the reaction mass, but rather that they are not needed. Suitable Cu(I) salts are CuCl, CuBr, CuI, CuF, CuCN, $CuNO_3$, and $CuCo_2R$, in which R is an alkyl or an aryl group containing up to 8 carbon atoms. A preferred $CuCO_2R$ salt is $CuC_2H_3O_2$. Particularly preferred salts are the Cu(I) halide salt with CuCl and CuBr being most preferred. CuCl is most highly preferred.

This copper, Cu(I) salts and mixtures thereof are used in catalytic quantities. Generally, the preferred amount used should provide at least about 200 parts per million parts of iron used in the reaction. Most highly preferred amounts are from about 300 parts to about 50,000 parts per million parts iron used in the reaction. Greater amounts can be used but are not believed to provide significantly higher yields of diphenylalkane product.

It is interesting to note that some commercial grades of iron powder are contaminated with Cu(I) salts and copper and that such powders can be used to supply the iron and at least part of the copper and/or Cu(I) salt requirements for the process of this invention. This finding is illustrated by Example I hereof.

The solvent used in the process of this invention is one in which Fe(II) halide is substantially soluble. Exemplary of suitable solvents are water, ethanol, and acetone. Water, the cheapest of these solvents, is preferred.

The solvent should be present in the reaction mass in a sufficient quantity to allow for a readily stirrable reaction mass and, preferably, to provide for the solubilization of substantially all of any Fe(II) halide salt formed during the process. When water is the solvent, there should be at least 10 mol of water per mol of phenylalkylhalide reactant to insure good yields. Very good diphenylalkane yields are obtained when from about 40 to about 75 mol of water are used per mol of phenylalkylhalide reactant.

The reaction mass is conveniently formed by adding the phenylalkylhalide to a mixture containing iron, the solvent, and the copper, Cu(I) salt or mixtures thereof. While this order of addition is preferred, it is to be understood that other addition orders may be utilized as the order of addition is not critical to the process of this invention.

The reaction mass, at least at its initial formation, is a heterogeneous mix. Therefore, to provide for optimum reaction conditions, it is desirable that the reaction mass be maintained in a mixed state to promote uniform distribution of the reaction mass constituents. It is to be understood that this uniformity can be achieved by conventional techniques, e.g. stirring, agitation, tumbling, etc.

It is preferred that the reaction mass be kept under a non-oxidizing atmosphere to prevent the formation of iron oxides. The formation of iron oxides is not desirable since the iron oxide is not capable of reagent activity in the reaction mass. Atmospheres of inert gases, e.g. nitrogen, argon, helium, etc., are suitable.

To obtain a reasonable reaction time, say 36 hours, the reaction mass should be maintained at a temperature of at least about 40° C. A preferred temperature is within the range of from about 80° C. to about 100° C. Temperature control can be easily effected by running the process under reflux conditions.

Maintenance of the reaction mass at the above-mentioned temperatures should be for a period of time which is at least sufficient to yield the diphenylalkane product. Generally, the higher the maintenance temperature, the shorter the reaction time required. It is preferred, from a process efficiency standpoint, that the temperature and the maintenance period be coordinated so that at least a 60% yield of the diphenylalkane product is obtained. With the maintenance temperature being within the range of from about 80° C. to 100° C., preferred maintenance times fall within the range of from about 3 hr to about 8 hr.

The pressure throughout the process of this invention is conveniently atmospheric, however, if the need should arise, sub- or super-atmospheric pressure can be used.

After the reaction mass has been maintained at the selected temperature and for the selected period of time, the diphenylalkane product can be removed therefrom. Depending upon the solvent used, the temperature of the reaction mass and the melting point of the particular diphenylalkane produced, the product can either be a solid, an immiscible liquid or in solution with the reaction mass solvent. If the product is a solid, it can be removed from the reaction mass by conventional liquid-solid separation techniques, e.g. filtration, centrifugation, etc. If the product is an immiscible liquid, techniques conventionally used in separating immiscible liquids can be used to recover the product, e.g. decantation, etc. In the case where the diphenylethane product is soluble in the solvent, such as can be the case when methanol is the solvent, product recovery is effected by evaporation of the solvent from the reaction mass.

If the diphenylalkane product is removed as a solid, it may contain some iron which then can be removed by solubilizing the soluble portions of the solid (principally diphenylalkane) with an alkanol, such as methanol. That portin of the solid which is not soluble in the alkanol, mostly iron, is then removed by conventional solid-liquid separation techniques, e.g. filtration, etc.

The following examples are provided to illustrate some of the features of the process of this invention. These examples are not to be taken as limiting the scope of the invention.

EXAMPLE I

A 250 ml, three necked, round-bottom flask was equipped with a mechanical stirrer, a reflux condenser, a thermometer, and an addition funnel. The flask was charged with water (120ml) and hydrogen-reduced 97% pure iron powder (5.5g, 0.1 mol). (The iron powder was obtained from Aldrich Chemical Company, Inc, and was stated to contain copper and Cu(I) salts.) The flask contents were heated and stirred under nitrogen to a temperature of 95° C. Benzyl chloride (25.3g, 0.2 mol) was then added in 2 min. The reaction mixture was stirred at 85° C. under nitrogen for 23 hr. The heating was discontinued and stirring was stopped. The contents were cooled with ice. The solid top layer formed after cooling was separated from the reaction mass by filtration. The solids contained iron which was removed by dissolving the alkanol-soluble solids in 100 ml of methanol. The iron was not soluble in the methanol and was removed therefrom by filtration. The remaining methanol solution was evaporated to yield pale yellow crystals weighing 11.4 g (62.6% yield). The melting point of the crystals was 48° C.–52° C. (Aldrich, pure diphenylethane mp is 50° C.). Gas chromatographic (G.C.) analysis showed the crystals to be 96.07% pure diphenylethane. Extraction of the filtrate (water from the original filtration) showed, by G.C. analysis, the presence of 96 area % benzyl alcohol, 2.4 area % diphenylethane, 0.3 area % dibenzyl ether, and 0.4 area % 3 benzyl-diphenylethane isomers.

EXAMPLE II

The procedure of Example I was repeated except that 150 ml of water were used and the reaction was allowed to proceed for 8 hr under nitrogen at 97° C.–98° C. The crystals (12.6 g) were determined by G. C. analysis to be 95.7% diphenylethane. The yield was 69.2%.

EXAMPLE III

The procedure of Example I was repeated except that benzyl chloride was added in 3 portions (10.7 g, 8.0 g, and 7.3 g) at 1.75 hr intervals and the total reaction time was only 6 hr at 85° C. The yield of diphenylethane was 9.9 g, i.e. a 54.4% yield.

EXAMPLE IV

The procedure of Example I was repeated except that the amount of iron powder was 11.0 g. After 25 hr at 95° C., 9.5 g of diphenylethane was obtained, i.e. a 52.2% yield.

EXAMPLE V

The procedure of Example I was repeated except that 200 ml of water were used and the reaction was run for 69 hr. The yield was 73.6% of 95% pure diphenylethane. The purity was determined by G.C. analysis.

EXAMPLE VI

The procedure of Example I was repeated except that the reaction mass contained 150 ml water, 5.6 g iron (99.9+% pure), 0.2 g CuCl (99.9% pure), and 25.4 g benzyl chloride. The reaction period was for 3 hr. 13.0 g of crude diphenylethane product was obtained. This represents a 71.4% yield.

EXAMPLE VII

The procedure of Example I was repeated except that the reaction mass contained 150 ml water, 5.6 g iron (97% pure), 0.11 g $Cu_2Br_2$ and 25.4 g or benzyl chloride. The $Cu_2Br_2$ used did not have a good color. The reaction period was for 3 hr. A crude diphenylethane product weighing 11.5 g was obtained. This represents a yield of 63%.

EXAMPLE VIII

The procedure of Example I was repeated except that the reaction mass contained 150 ml water, 5.6 g iron powder (99.9+% pure), 0.028 g copper and 0.028 g CuCl. The reaction period was for 4 hr. A crude diphenylethane product was recovered weighing 14.6 g representing an 80.2% yield. The product was found by G.C. analysis to contain 98.7 area % diphenylethane, 0.4 area % benzyl alcohol, and 0.6 area % benzyl-diphenylethane isomers.

EXAMPLE IX

The procedure of Example I was repeated except that the reaction mass contained 150 ml water, 5.6 g iron (99.9+% pure), 0.20 g copper powder, 0.13 g CuCl, and 25.6 g benzyl chloride. The reaction period was 4 hr. The crude diphenylethane product obtained weighed 15.3 g which represents an 84.06% yield. By G.C. analysis, the product contained 97.9 area % diphenylethane, 1.4 area % benzyl-diphenylethane isomers, and 0.6 area % unknowns.

EXAMPLE X

The procedure of Example I was repeated except that the reaction mass contained 150 ml water, 5.6 g iron (97% pure), 0.14 g copper powder, 0.14 g CuCl, and 25.6 g benzyl chloride. The reaction time was 3 hr. After the reaction was completed, the reaction mass was allowed to stand overnight. The weight of the crude diphenylethane product obtained was 12.6 g which represents an 69.2% yield. It is believed that this relatively low yield was the result of utilizing a partially oxidized CuCl reagent. Partial oxidation was suspected because the CuCl had a green tint.

EXAMPLE XI

The procedure of Example I was repeated except that the reaction mass contained 150 ml water, 5.6 g iron powder (99.9+% pure) 0.15 g copper powder, 0.15 g CuCl, and 25.4 g benzyl chloride. The reaction time was 6 hr. A crude diphenylethane product weighing 15.2 g was obtained. Such a recovery represents an 83.5% yield.

EXAMPLE XII

A 250 ml, three necked, round-bottom flask was equipped with a mechanical stirrer, a reflux condenser, a thermometer, and an addition funnel. The flask was charged with 150 ml of water and 5.7 g of hydrogen-reduced iron powder, which was 99.9+% pure and obtained from Aldrich Chemical Company, Inc. The flask contents were heated and stirred under nitrogen to a temperature of about 95° C. 25.4 g of benzyl chloride was then added and the reaction mass was maintained at a temperature of about 95° C. for 7 hr. After the reaction period the reaction slurry was allowed to stand and cool overnight. After standing no crystals were noted to have been formed. The reaction mass was then extracted twice with 50 ml methylene chloride and dried over anhydrous sodium sulfate. After filtration, the methylene chloride solution showed, by G.C. analysis, to be a mixture of diphenylethane (39.8 area %) and benzyl alcohol (56.7 area %). Upon the slow evaporation of the methylene chloride solvent the formation of white crystals of diphenylethane was noted. The recovered white crystals of diphenylethane weighed 3.0 g. A colorless, oily liquid which was also recovered weighed 8.0 g. The 3.0 g of diphenylethane represents a 16.48% yield.

EXAMPLE XIII

In the same equipment utilized in Example XII was placed 150 ml of water and 12.7 g (0.2 mol) of copper powder. To the flask was then added 25.3 g of benzyl chloride (0.2 mol). The reaction mass was maintained at a temperature of 100° C. under nitrogen for 3.5 hr. After the reaction period the reaction mass was allowed to cool and left to stand overnight. After cooling and standing the reaction mass was found to contain a brown solid and two liquid phases. The solid weighed 12.5 g and was believed to be unreacted copper metal. There were two liquid phases, an organic phase and an aqueous phase. These two phases were separated. The organic phase weighed 10.9 g and smelled similar to benzyl alcohol. The aqueous did not contain any detectable amounts of diphenylethane.

EXAMPLE XIV

The equipment of Example XII was used. Into the flask was place 150 ml of water, 19.8 g (0.2 mol) of CuCl. The ingredients of the flask were then heated to 100° C. under nitrogen with stirring. The originally mustard-colored solution became brick-red at 100° C. 25.3 g (0.2 mol) of benzyl chloride was added and stirred. The solution was stirred at 100° C. for 3 hr. Approximately 10 minutes after the addition of the benzyl chloride, the brick-red solution turned to a light gray. When the reaction period was complete the contents were allowed to cool. A solid phase and a liquid phase were obtained. The liquid phase consisted of an organic layer and an aqueous layer. The reaction mass was filtered. The recovered solids were extracted with 50 ml of methylene chloride. The solids were then washed with 25 ml of additional methylene chloride. The washings were evaporated to yield a yellow oil (3.3 g). No diphenylethane was detected. The liquid phase was extracted twice with 50 ml of methylene chloride. Methylene chloride was evaporated from the solution. The evaporation occurred overnight at room temperature. A yellow-green liquid weighing 11.0 g was recovered. No diphenylethane was found in the yellow-green liquid.

In Example XII, the utilization of iron alone gave a low yield of diphenylethane. In Example XIII, copper, in the absence of iron, was used and no diphenylethane was detected. In Example XIV, iron was absent and CuCl was used. In this example the production of diphenylethane was not seen. It is therefore surprising that the combination of iron and copper and/or a Cu(I) salt results in high yields of diphenylalkane.

What is claimed:

1. A process for preparing diphenylalkanes of the formula,

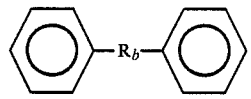

wherein R is a methylene group and b is 2, 4, 6, 8, or 10, which process comprises:
 (a) forming a reaction mass which initially contains,
  (i) iron,
  (ii) a catalytic quantity of copper, a Cu(I) salt of an inorganic or organic acid or a mixture of copper and said Cu(I) salt,
  (iii) a phenylalkylhalide of the formula,

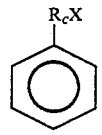

wherein R is a methylene group, $c = \frac{1}{2} b$ and X is a halide radical,
  (iv) a solvent in which Fe(II) halide is substantially soluble, and
 (b) maintaining said reaction mass at a temperature of at least 40° C. until said diphenylalkane is formed.
2. The process of claim 1 wherein b is 2.
3. The process of claim 1 wherein X is chlorine.
4. The process of claim 2 wherein X is chlorine.
5. The process of claim 1 wherein said solvent is water.
6. The process of claim 5 wherein there is at least about 10 mol of water per mol of phenylalkylhalide.
7. The process of claim 1 wherein said Cu(I) salt is a Cu(I) halide salt.
8. The process of claim ( wherein said Cu(I) halide salt is CuCl.
9. The process of claim 1 wherein there are at least 200 parts of said copper, Cu(I) halide salt or said mixture of copper and Cu(I) salt in the reaction mass per million parts of iron used in the reaction.
10. The process of claim 1 wherein there is, initially present in the reaction mass, at least 0.50 mol of iron per mol of phenylalkylhalide.
11. The process of claim 1 wherein said temperature is within the range of from about 80° C. to about 100° C.
12. The process of claim 1 wherein reaction mass is maintained at said temperature until at least a 60% yield of said diphenylalkane is obtained, said yield being based upon the amount of said phenyllalkylhalide initially present in the reaction mass.
13. The process of claim 1 wherein said reaction mass is maintained at said temperature for a period of time within the range of from about 3 hr to about 8 hr.
14. The process of claim 1 wherein said diphenylalkane is recovered from said reaction mass.
15. The process of claim 1 wherein a product containing iron impurities and said diphenylalkane is recovered from said reaction mass after (b) and said product is treated after recovery to reduce the amount of said iron impurities contained therein.
16. A process for preparing diphenylalkanes of the formula,

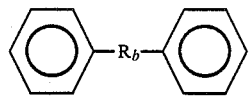

wherein R is a methylene group and b is 2, 4, 6, 8, or 10, which process comprises:
 (a) forming a reaction mass which initially contains,
  (i) a phenylalkylhalide of the formula,

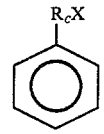

wherein R is a methylene group, $c = \frac{1}{2} b$ and X is a chlorine or bromine,
  (ii) at least about 0.50 mol of iron per mol of said phenylalkylhalide,
  (iii) at least about 10 mol of water per mol of said phenylalkylhalide,
  (iv) at least about 200 parts of copper, Cu(I) halide salt or a mixture of copper and Cu(I) halide salt per million parts of iron used in the reaction; and
 (b) maintaining said reaction mass at a temperature of at least 40° C. until said diphenylalkane is formed.
17. The process of claim 18 wherein b is 2.
18. The process of claim 17 wherein X is chlorine.
19. The process of claim 18 wherein said Cu(I) halide salt is CuCl.
20. The process of claim 19 wherein said temperature is within the range of from about 80° C. to about 100° C.
21. The process of claim 20 wherein reaction mass is maintained at said temperature until at least a 60% yield of said diphenylalkane is obtained, said yield being based upon the amount of said phenylalkylhalide.

* * * * *

UNITED STATES PATENT AND TRADEMARK OFFICE
CERTIFICATE OF CORRECTION

PATENT NO. : 4,929,785

DATED : MAY 29, 1990

INVENTOR(S) : SAADAT HUSSAIN

It is certified that error appears in the above-identified patent and that said Letters Patent is hereby corrected as shown below:

Column 7, line 62 reads "Claim (" and should read -- Claim 7 -- .

Column 8, line 11 reads "phenyllalkylhalide" and should read -- phenylalkylhalide -- .

Column 8, line 55 reads "Claim 18" and should read -- Claim 16 -- .

Signed and Sealed this

Seventeenth Day of September, 1991

Attest:

HARRY F. MANBECK, JR.

*Attesting Officer*  *Commissioner of Patents and Trademarks*